United States Patent [19]

Girijavallabhan et al.

[11] 4,431,654
[45] Feb. 14, 1984

[54] 6-(HYDROXYETHYL)-2-[(HETEROCYCLYL OR ARYL)THIOALKYLTHIO]-PENEM-3-CARBOXYLATES

[75] Inventors: Viyyoor M. Girijavallabhan, Parsippany; Ashit K. Ganguly, Upper Montclair; Naginbhai M. Patel, Kearny; Yi-Tsung Liu, Parsippany, all of N.J.

[73] Assignee: Schering Corporation, Kenilworth, N.J.

[21] Appl. No.: 365,427

[22] Filed: Apr. 5, 1982

[51] Int. Cl.³ ............... C07D 499/00; A61K 31/425
[52] U.S. Cl. .......................... 424/270; 260/245.2 R
[58] Field of Search ................ 260/245.2 R; 424/270

[56] References Cited

U.S. PATENT DOCUMENTS 4,260,618  4/1981  Christensen et al. ........ 260/245.2 R

FOREIGN PATENT DOCUMENTS 17992  10/1980  European Pat. Off.
55-153789  11/1980  Japan.

*Primary Examiner*—Nicholas S. Rizzo
*Attorney, Agent, or Firm*—Gerald S. Rosen; Bruce M. Eisen

[57] ABSTRACT

There are disclosed antibacterially effective compounds represented by the formula

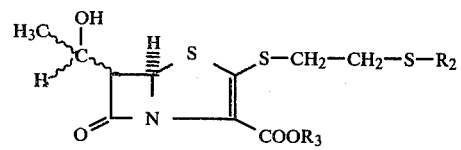

wherein $R_2$ represents a substituted or unsubstituted single ring or double fused ring aryl or heterocyclyl radical bonded to the sulfur atom by a ring carbon, selected from the group consisting of phenyl, naphthyl, benzothiazolyl, oxazinyl, pyridyl, purinyl, imidazolyl, pyrryl, thiazolyl, thiadiazolyl, benzimidazolyl, triazinyl, furyl, thienyl, thiazinyl, triazolyl, tetrazolyl and pyrimidyl, wherein when substituted, said aryl or heterocyclic rings have one or more substituent which can be the same or different (a) are on a ring carbon or heteroatom, and are independently selected from the group consisting of lower alkyl,

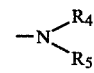

and loweralkylene

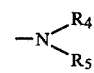

wherein $R_4$ and $R_5$ are the same or different and are independently selected from the group consisting of hydrogen, halogen and lower alkyl or (b) are on a ring carbon atom only and are selected from the group consisting of =O, hydroxy, lower alkoxy, —COOR₃ or halogen; wherein $R_3$ represents hydrogen, a pharmaceutically acceptable readily metabolizable ester-forming substituent or a pharmaceutically acceptable cation, and the wavy line represents the 5R,6S,8R and 5R,6R,8S stereoisomers; and novel intermediates, processes and antibacterial pharmaceutical and veterinary compositions thereof.

14 Claims, No Drawings

6-(HYDROXYETHYL)-2-[(HETEROCYCLYL OR ARYL)THIOALKYLTHIO]-PENEM-3-CARBOXYLATES

SUMMARY

This invention relates to certain novel isomers of 5R,6S,8R and 5R,6R,8S 6-(hydroxyethyl-2-[(heterocyclyl or aryl)thioalkylene-thio]-penem-3-carboxylates which possess antibacterial activity, pharmaceutical compositions thereof, novel processes and intermediates for making said compounds as well as methods for treating bacterial infections utilizing said compounds.

More particularly, this invention relates to compounds represented by the following formula I

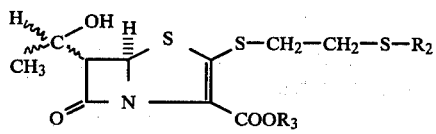

wherein $R_2$ represents a substituted or unsubstituted single ring or double fused ring aryl or heterocyclyl radical bonded to the sulfur atom by a ring carbon, selected from the group consisting of phenyl, naphthyl, benzothiazolyl, oxazinyl, pyridyl, purinyl, imidazolyl, pyrryl, thiazolyl, thiadiazolyl, benzimidazolyl, triazinyl, thiazinyl, furyl, thienyl, triazolyl, tetrazolyl and pyrimidyl, wherein when substituted, said aryl or heterocyclic rings have one or more substituent which can be the same or different and (a) are on a ring carbon or heteroatom, and are independently selected from the group consisting of lower alkyl,

and loweralkylene

wherein $R_4$ and $R_5$ are the same or different and are independently selected from the group consisting of hydrogen, halogen and lower alkyl or (b) are on a ring carbon atom only and are selected from the group consisting of =O, hydroxy, lower alkoxy, —$COOR_3$ or halogen;

$R_3$ represents hydrogen, a pharmaceutically acceptable readily metabolizable ester forming substituent or a pharmaceutically acceptable cation; and the wavy line indicates either the 5R,6S,8R or 5R,6R,8S stereoisomers.

As used herein, "lower alkyl" when used alone or in combination with another moiety means straight and branched chain alkyl groups having from 1 to 6 carbon atoms, e.g. methyl, ethyl, n-propyl, iso-propyl, butyl, t-butyl, pentyl, hexyl and the like; "lower alkylene" means straight or branched chain alkylene groups having from 1 to 6 carbon atoms, e.g. methylene (—$CH_2$—), ethylene (—$CH_2$—$CH_2$—), trimethylene (—$CH_2$—$CH_2$—$CH_2$—) and the like;

The heterocyclyl radicals of $R_2$ include their substituted and isomeric forms, e.g. 2-benzothiazole, 2-pyridyl, 4-pyridyl, 2-purinyl, 4-purinyl, 8-purinyl, 2-imidazolyl, 1-lower alkyl-2-imidazolyl, 4-lower alkyl-2-imidazolyl, 5-lower alkyl-2-imidazolyl, 4- or 5-lower alkyl-2(1,3,4-thiadiazolyl), 4,5-dihydroxy-2-imidazolyl, 1-lower alkyl-4,5-dioxo-2-imidazolyl, 5,6-dioxo-3-(1,2,4-triazinyl), 2-lower alkyl-5,6-dioxo-5-(1-lower alkyl-1,2,3-triazolyl), 5-(1,2,3,4-tetrazolyl), 2-furyl, 3-furyl, 2-thienyl, 3-thienyl, 2-pyrryl, 3-pyrryl, 5-(1-lower-alkyl-1,2,3,4-tetrazolyl), 5-[1-(2-dimethylaminoethyl)-1,2,3,4-tetrazolyl], 2-pyrimidyl, 4-pyrimidyl and the like.

"Halogen" as used herein includes chlorine, fluorine and bromine; "lower alkoxy" means alkoxy radicals containing straight and branched chain alkyl groups of from 1 to 6 carbons, e.g. methoxy, ethoxy, isopropoxy, butoxy and the like. "A pharmaceutically acceptable readily metabolizable ester forming substituent" includes substituents which form with a carboxyl group, esters readily hydrolyzable in vivo. These esters are an art recognized class of compounds, the most prominent groups of which are, e.g. acetoxymethyl, pivaloyloxymethyl, alpha-ethoxycarbonyloxyethyl, phthalidyl, (2-oxo-5-phenyl-1,3-dioxolen-4-yl) methyl, and the like. The substituents preferred for this invention are the readily available pivaloyloxymethyl and the phthalidyl groups.

"A pharmaceutically acceptable cation" means alkali metals such as sodium and potassium, alkaline earth metals such as calcium and magnesium, as well as ammonium cations such as N-methylglucamine, pyridinium, triethyl ammonium, triethanol ammonium or ammonium. The preferred salts are the potassium and sodium salts. The salts can be single or double salts, e.g. when —$COOR_3$ is a ring substituent at $R_2$, the compounds can be double salts such as the disodium salt. The $R_3$ substituent on the ring carboxyl substituent at the 2-position can be different than the $R_3$ substituent at the 3-position, e.g. $R_3$ on the ring carboxyl substituent at the 2-position can be hydrogen and $R_3$ at the 3-position can be sodium.

The preferred compounds of this invention are the 5R,6S,8R stereoisomers of formula I represented by the following formula II

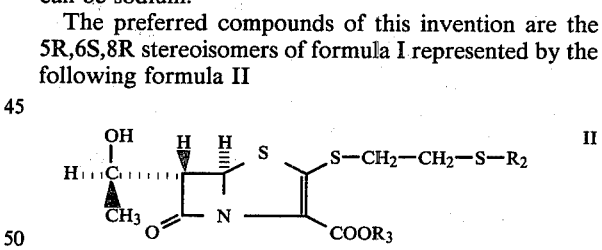

wherein $R_2$ and $R_3$ are as defined in formula I.

The preferred compounds of formula II are those in which $R_2$ is selected from the group consisting of 2-benzothiazole, 2-pyridyl, 4-pyridyl, 2-purinyl, 4-purinyl, 8-purinyl, 2-imidazolyl, 1-lower alkyl-2-imidazolyl, 4-lower alkyl-2-imidazolyl, 5-loweralkyl-2imidazolyl, 4-lower alkyl-2-(1,3,4-thiadiazolyl), 5-lower alkyl-2-(1,3,4-thiadiazolyl), 4,5-dihydroxy-2imidazolyl, 1-lower alkyl-4,5-dioxo-2-imidazolyl, 5,6-dioxo-3-(1,2,4-triazinyl), 2-lower alkyl-5,6-dioxo5-(1-lower alkyl-1,2,3-triazolyl), 5-(1,2,3,4-tetrazolyl), 5-(1-lower alkyl-1,2,3,4-tetrazolyl), 5-[1-(2-dimethyl-aminoethyl)-1,2,3,4-tetrazolyl],2-pyrimidyl, 4-pyrimidyl, parahydroxyphenyl, ortho-hydroxyphenyl, para-aminophenyl, ortho-aminophenyl, para-carboxyphenyl and paradimethylaminophenyl; and $R_3$ represents sodium, potassium phthalidyl or pivaloyloxymethyl.

The compounds of this invention possess gram-positive and gram-negative activity. The most preferred compounds of this invention exhibit both gram-positive and gram-negative activity while others exhibit excellent gram-positive activity. Most importantly, they are orally active antibacterial agents which afford good blood levels at antibacterial dosages. When tested in standardized microbiological assays, the compounds of this invention are active against such gram-positive organisms as *Straphylococcus aureus,* and *Sarcina lutea* and such gram-negative organisms as *Klebsiella pneumoniae* and Providencia at test levels of 0.1 to 100 micrograms per milliliter on Mueller-Hinton Agar-pH 7.4. Additionally, they display low protein binding and show stability and activity against organisms which produce beta-lactamases, indicating a resistance against these enzymes. For example sodium (5R,6S,8R)-2-[2-(5-(1-methyltetrazolyl)thio]ethylthio-6-(1-hydroxyethyl)-penem-3-carboxylate is active against *Staphylococcus aureus* #76050601 at a test level of 0.06251 micrograms per milliliter and *K. pneumoniae* #00GT3020 at a test level of 0.500 micrograms per milliliter.

The compounds of this invention are useful for treating warm blooded animals (including humans) having a susceptible bacterial infection. The compounds can be administered orally, parenterally and topically. In addition, the compounds can be used to sterilize materials which are contaminated by susceptible bacteria, e.g. medical and dental instruments.

Thus, the present invention includes within its scope non-toxic compositions suitable for pharmaceutical, veterinary and decontamination uses comprising an antibacterially effective amount of a penem of formula I together with a compatible non-toxic carrier or coating acceptable for the intended use, e.g. pharmaceutical, veterinary or decontamination. Also included within this invention is the method of effectively treating a warm blooded animal having a susceptible bacterial infection which comprises administering to said animal a non-toxic, antibacterially effective amount of a compound of formula I. A preferred pharmaceutical composition is an oral dosage from comprising an antibacterially effective amount of a compound of formula II, particularly those wherein $R_3$ is a pharmaceutically acceptable cation, together with a veterinary or pharmaceutically acceptable carrier. Of these oral compositions, those which are solid, e.g. tablets or capsules, are particularly useful.

The dosage of the penems of this invention administered is dependent upon the age and weight of the animal species being treated, the exact mode of aministration, and the type and severity of bacterial infection being prevented or reduced. The dosage administered per day is within the judgment of the attending clinician but typically, for humans will be in the range of 100–5000 mg., preferably with 500–1000 mg. being administered two to four times, a day.

For oral administration, the compounds of this invention may be formulated, using conventional pharmaceutical and veterinary excipients and carriers in the form of tablets, capsules, elixirs, boluses or the like. Likewise, they may be admixed with animal feed or drinking water. They may also be applied topically in the form of ointments, both hydrophilic and hydrophobic, in the form of lotions which may be aqueous, non-aqueous or of the emulsion type, or in the form of creams all compounded with conventional pharmaceutical excipients and carriers.

The compounds of formula I may be utilized in liquid form such as solutions, suspensions, and the like for otic and optic use and may also be administered parenterally via intramuscular injection. All dosage forms can be compounded with conventional pharmaceutical excipients and carriers.

The preferred compositions of this invention are oral dosage forms of the preferred compounds of formula II. Preferably the compounds are administered as the mono-sodium salt. When the compounds are orally administered they exhibit an unusual combination of high potency of prolonged duration, broad anti-bacterial spectrum and efficacy.

The compounds of this invention can be prepared by a number of reaction sequences. The stereoisomers of formula I are preferably made by utilizing the appropriate stereoisomeric starting compounds in the hereinafter described processes of this invention. For convenience, the preparations of the preferred 5R,6S,8R stereoisomers are described. The preferred reactions are novel and the starting materials used in them are (5R,6R,8S) or (5R,6S,8R) allyl-6-hydroxyethyl-2-(hydroxyalkylene)thiopenem-3-carboxylates. These starting materials are prepared according to the methods described in European Patent Office published application No. 0013662 (application number 80810004.4), the disclosure of which is incorporated by reference herein.

The compounds of this invention can readily be prepared as follows:

METHOD A. Mixing together in approximately equimolar amounts, the following reagents, (a) dilower alkyl azodicarboxylate, (b) triarylphosphine or triloweralkylphosphine, (c) allyl-(5R,6S,8R)-6-hydroxyethyl-2-(hydroxyethyl)thiopenem-3-carboxylate wherein the carboxy group and all the hydroxy groups are protected except the hydroxy group at the 2-position, and (d) $R_2$—SH wherein $R_2$ is as defined in formula I.

The preferred reactants are (a) diethyl azodicarboxylate, (b) triphenylphosphine. Both reagent (a) and reagent (b) are disclosed in Mitsunobu, Synthesis, page 1, January, 1981; (c) allyl-(5R,6S,8R)-2-(2-hydroxyethylenethio)-6-(1-trichloroethoxycarbonyloxyethyl)-penem-3-carboxylate; and (d) $R_2$—SH wherein $R_2$ is as defined in formula I.

The reactants are mixed together in an organic solvent which is inert under the reaction conditions. Typical suitable solvents are methylene chloride, benzene, toluene, dimethyl formamide (DMF) and the like. Preferred is methylene chloride. The reaction takes place at about 0° C. to about 25° C. when the reactant (b) phosphine is the preferred triphenyl phosphine. If a triloweralkyl phosphine, e.g. tributyl phosphine is used, then the reaction temperature is from about −20° C. to about 0° C. The pH of the reaction mixture is essentially neutral and the reaction takes about ½ to 20 hours. Completion of the reaction is shown on TLC (thin layer chromatography). The yields are high.

Once this reaction is completed, the resulting product, which still has the protecting groups on the 6-hydroxy and the 3-carboxyl groups, is deprotected by conventional means to yield compounds of formula I. Hydrogenation can be used to remove the protecting groups, e.g. benzyloxycarbonyl, paranitrobenzyloxy carbonyl, benzyhydryloxycarboxyl, benzyl, paranitrobenzyl and benzhydryl. Others such as trichloroethoxycarbonyl can be removed via zinc/acetic acid in tetrahydrofuran (THF). The allyl group can be removed by the process taught in commonly assigned U.S. patent application Ser. No. 2,472 filed Jan. 10, 1979, e.g. by reaction with sodium 2-ethylhexanoate followed by triphenylphosphine and a palladium(O) catalyst reagent, under an inert argon atmosphere.

The hydroxy and carboxyl protected intermediates are novel compounds and are represented by the following formula III

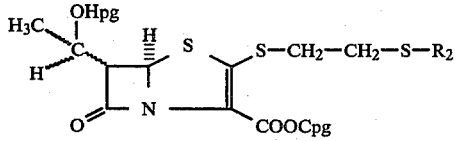

wherein $R_2$ and the wavy lines are as defined in formula I, Cpg represents a readily removable carboxylprotecting group and Hpg represents a readily removable hydroxyprotecting group.

As used herein "Carboxylprotecting group" means conventional carboxyl-protectors such as allyl, p-nitrobenzyl, benzyl or benzhydryl, with allyl preferred.

As used herein "Hydroxyprotecting group" means conventional readily removable groups such as, e.g. 2,2,2-trichloroethoxycarbonyl, 1,1,1-trichloro-2-methyl-2-propoxycarbonyl, para-nitrobenzyloxycarbonyl, allyloxycarbonyl or beta-trimethylsilylethoxycarbonyl, with 2,2,2-trichloroethoxycarbonyl being preferred.

The preferred compounds of formula III are the 5R,6S,8R stereoisomers.

A second method for preparing the compounds of formula I is as follows:

METHOD B. Mixing together in approximately equimolar amounts, the same hydroxypenem as in method A with a disulfide in the presence of a methylene chloride solvent and tri-n-butylphosphine. The disulfide can be a diheterocyclyl or diaryl disulfide wherein the heterocyclyl or diaryl moieties are the same as those in the definition of $R_2$, the preferred disulfide is diphenyl disulfide. The disulfide-tri-n-butylphosphine reactant is disclosed in J. Am. Chem. Soc. 103 No. 20, 224 (1981).

The reaction takes place at from about 0° C. to 25° C. (room temperature) and is completed, with high yields, in from about ½ to about 20 hours. The completion of the reaction is determined by TLC. The resulting product is a compound of formula III. It is deprotected as discussed above to result in the compounds of formula I.

In reaction B, the disulfide can be replaced by equimolar amounts of $R_2$—SX wherein $R_2$ is as defined in formula I and X is halogen, e.g. chlorine.

A third method for preparing the compounds of formula I is as follows:

METHOD C. Mixing together in approximately equimolar amounts, the same hydroxypenem as in METHODS A and B with bis (2,2,2-trifluoroethoxy)-triphenyl phosphorane and $R_2SH$, wherein $R_2$ is as defined in formula I, at from about 0° C. to 25° C. (room temperature) and the reaction is completed, with high yields, in about ½ to about 20 hours. The completion of the reaction is determined by TLC. The resulting product is a compound of formula III. It is deprotected as discussed above to result in the compounds of formula I.

A fourth method for preparing the compounds of formula I is as follows:

METHOD D. Mixing together in approximately equimolar amounts, the same hydroxypenem as in METHODS A, B and C with pyridine and trifluoromethane sulfonic anhydride followed by the thiol $R_2SH$ wherein $R_2$ is as defined in formula I, at about −20° C. The reaction is completed in about 1 to 4 hours in high yield. The resulting product is a compound of formula II which is subsequently deprotected as discussed above to yield a compound of formula I.

Using the described processes, the following compounds within the scope of this invention can be made.

1. Sodium (5R,6S,8R)-2-[2-(5-(1-methyl)tetrazolyl)thio]-ethylthio-6-(1-hydroxyethyl)penem-3-carboxylate.
2. Sodium (5R,6S,8R)-2-[2-(5-(1-β-dimethylaminoethyl)tetrazolyl)thio]ethylthio-6-(1-hydroxyethyl)-penem-3-carboxylate.
3. Sodium (5R,6S,8R)-2-[2-(5-(1-carboxymethyl)tetrazolyl))thio]-ethylthio-6-(1-hydroxyethyl)penem-3-carboxylate.
4. Sodium (5R,6S,8R)-2-[2-(5-(1-ethyl)tetrazolyl))thio]ethylthio-6-(1-hydroxyethyl)penem-3-carboxylate.
5. Sodium (5R,6S,8R)-2-[2-(5-tetrazolyl))thio]-ethylthio-6-(1-hydroxyethyl)penem-3-carboxylate.
6. Sodium (5R,6S,8R)-2-[2-((2-benzo)thiazolyl))thio]ethylthio-6-(1-hydroxyethyl)penem-3-carboxylate.
7. Sodium (5R,6S,8R)-2-[2-((2-thiazolyl))thio]ethylthio-6-(1-hydroxyethyl)penem-3-carboxylate.
8. Sodium (5R,6S,8R)-2-[2-(5-thiazolyl))thio]-ethylthio-6-(1-hydroxyethyl)penem-3-carboxylate.
9. Sodium (5R,6S,8R)-2-[2-((4-thiazolyl))thio]ethylthio-6-(1-hydroxyethyl)penem-3-carboxylate.
10. Sodium (5R,6S,8R)-2-[2-(2-(pyridyl))thio]ethylthio-6-(1-hydroxyethyl)penem-3-carboxylate.
11. Sodium (5R,6S,8R)-2-[2-((4-pyridyl))thio]ethylthio-6-(1-hydroxyethyl)penem-3-carboxylate.
12. Sodium (5R,6S,8R)-2-2-[2-(3-hydroxy)pyridyl)thio]-ethylthio-6-(1-hydroxyethyl)penem-3-carboxylate.
13. Sodium (5R,6S,8R)-2-2-[2-(4-hydroxy)pyridyl)thio]-ethylthio-6-(1-hydroxyethyl)penem-3-carboxylate.
14. Sodium (5R,6S,8R)-2-2-[2-(6-hydroxy)pyridyl)thio]-ethylthio-6-(1-hydroxyethyl)penem-3-carboxylate.
15. Sodium (5R,6S,8R)-2-2-[2-(3-amino)pyridyl)]thio-6-(1-hydroxyethyl)penem-3-carboxylate.
16. Sodium (5R,6S,8R)-2-2-[2-(4-amino)pyridyl)thio]-ethylthio-6-(1-hydroxyethyl)penem-3-carboxylate.
17. Sodium (5R,6S,8R)-2-2-[2-(6-amino)pyridyl)thio]-ethylthio-6-(1-hydroxyethyl)penem-3-carboxylate.
18. Sodium (5R,6S,8R)-2-2-[(4-(2-hydroxy)pyridyl)thio]-ethylthio-6-(1-hydroxyethyl)penem-3-carboxylate.
19. Sodium (5R,6S,8R)-2-2-[(4-(2-amino)pyridyl]thio-6-(1-hydroxyethyl)penem-3-carboxylate.
20. Sodium (5R,6S,8R)-2-[2-(2-purinyl)thio]ethylthio-6-(1-hydroxyethyl)penem-3-carboxylate.
21. Sodium (5R,6S,8R)-2-2-[2-(4-hydroxy)purinylthio]-ethylthio-6-(1-hydroxyethyl)penem-3-carboxylate.
22. Sodium (5R,6S,8R)-2-2-[2-(8-hydroxy)purinylthio]-ethylthio-6-(1-hydroxyethyl)penem-3-carboxylate.
23. Sodium (5R,6S,8R)-2-2-[2-(4-amino)purinylthio]-ethylthio-6-(1-hydroxyethyl)penem-3-carboxylate.
24. Sodium (5R,6S,8R)-2-2-[2-(8-amino)purinylthio]-ethylthio-6-(1-hydroxyethyl)penem-3-carboxylate.
25. Sodium (5R,6S,8R)-2-[2-(8-purinyl)thio]-ethylthio-6-(1-hydroxyethyl)penem-3-carboxylate.
26. Sodium (5R,6S,8R)-2-2-[8-(2-hydroxy)purinylthio]-ethylthio-6-(1-hydroxyethyl)penem-3-carboxylate.
27. Sodium (5R,6S,8R)-2-2-[8-(4-hydroxy)purinylthio]-ethylthio-6-(1-hydroxyethyl)penem-3-carboxylate.
28. Sodium (5R,6S,8R)-2-2-[8-(2-amino)purinylthio]-ethylthio-6-(1-hydroxyethyl)penem-3-carboxylate.
29. Sodium (5R,6S,8R)-2-2-[8-(4-amino)purinylthio]-ethylthio-6-(1-hydroxyethyl)penem-3-carboxylate.

30. Sodium (5R,6S,8R)-2-[2-(2-imidazolyl)thio]ethylthio-6-(1-hydroxyethyl)penem-3-carboxylate.
31. Sodium (5R,6S,8R)-2-[2-(2-imidazolyl)thio]ethylthio-6-(1-hydroxyethyl)penem-3-carboxylate.
32. Sodium (5R,6S,8R)-2-2-[2-(1,3,4 thiadiazolyl)thio]-ethylthio-6-(1-hydroxyethyl)penem-3-carboxylate.
33. Sodium (5R,6S,8R)-2-2-[2-(3-methyl)1,3,4 thiadiazolylthio]-ethylthio-6-(1-hydroxyethyl)penem-3-carboxylate.
34. Sodium (5R,6S,8R)-2-2-[2-(4,5 dihydroxy 1-methyl)imidazolylthio]-ethylthio-6-(1-hydroxyethyl)penem-3-carboxylate.
35. Sodium (5R,6S,8R)-2-2-[3-(5,6 dioxo)1-2-4-triazinylthio]-ethylthio-6-(1-hydroxyethyl)penem-3-carboxylate.
36. Sodium (5R,6S,8R)-2-{2-[3-(5,6 dioxo) 2-methyl 1,2,6-triazinyl]thio}ethylthio-6-(1-hydroxyethyl)-penem-3-carboxylate.
37. Sodium (5R,6S,8R)-2-[2-(4-1,2,3-triazolyl)thio]ethylthio-6-(1-hydroxyethyl)penem-3-carboxylate.
38. Sodium (5R,6S,8R)-2-[2-(5-1,2,3-triazolyl)thio]ethylthio-6-(1-hydroxyethyl)penem-3-carboxylate.
39. Sodium (5R,6S,8R)-2-[2-(2-pyrimidyl)thio]ethylthio-6-(1-hydroxyethyl)penem-3-carboxylate.
40. Sodium (5R,6S,8R)-2-{2-[2-(4-hydroxy)pyrimidyl]thio}ethylthio-6-(1-hydroxyethyl)penem-3-carboxylate.
41. Sodium (5R,6S,8R)-2-{2-[2-(6-hydroxy)pyrimidyl]thio}ethylthio-6-(1-hydroxyethyl)penem-3-carboxylate.
42. Sodium (5R,6S,8R)-2-{2-[2-(4-amino)pyrimidyl]thio}ethylthio-6-(1-hydroxyethyl)penem-3-carboxylate.
43. Sodium (5R,6S,8R)-2-{2-[2-(6-amino)pyrimidyl]thio}ethylthio-6-(1-hydroxyethyl)penem-3-carboxylate.
44. Sodium (5R,6S,8R)-2-[2-(2-furyl)thio]ethylthio-6-(1-hydroxyethyl)penem-3-carboxylate.
45. Sodium (5R,6S,8R)-2-[2-(2-thienyl)thio]ethylthio-6-(-hydroxyethyl)penem-3-carboxylate.
46. Sodium (5R,6S,8R)-2-[2-(2-pyrryl)thio]ethylthio-6-(1-hydroxyethyl)penem-3-carboxylate.
47. Sodium (5R,6S,8R)-2-{2-[2-(benzimidazolyl)]thio}ethylthio-6-(1-hydroxyethyl)penem-3-carboxylate.
48. Sodium (5R,6S,8R)2-(2-phenylthio)ethylthio-6-(1-hydroxyethyl)penem-3-carboxylate.
49. Sodium (5R,6S,8R)-2-[2-(2-hydroxyphenyl)thio]ethylthio-6-(1-hydroxyethyl)penem-3-carboxylate.
50. Sodium (5R,6S,8R)-2-[2-(2-oxazinyl)thio]ethylthio-6-(1-hydroxyethyl)penem-3-carboxylate.
51. Sodium (5R,6S,8R)-2-(2-naphthylthio)ethylthio-6-(1-hydroxyethyl)penem-3-carboxylate.

The following examples illustrate the preparation of compounds and compositions of the invention. All temperatures are in °Celsius.

EXAMPLE 1

Sodium (5R,6S,8R)-2-[2-(2-benzothiazole)-thio]ethylthio-6-(1-hydroxyethyl)-penem-3-carboxylate (a) At room temperature, with stirring, add 0.025 ml diethylazidocarboxylate to a solution of 50 mg (5R,6S,8R)-2-(2-hydroxyethyl)thio-6-(1-trichloroethoxycarbonyloxyethyl)-penem-3-carboxylate and 20 mg of benzothiazole thiol in 4 ml dry methylenechloride, then add 0.05 ml of tri-normalbutylphosphine. Test the reaction for completeness after ½ hour by TLC (5% ethylacetate CH$_2$Cl$_2$). The product which results is allyl 5R,6S,8R-2-[2-(2-benzothiazole)thio]ethylthio-6-(1-trichloro-ethoxycarbonyloxyethyl)-penem-3-carboxylate, then deprotect the product, first at the hydroxy group, then at the carboxyl group as follows:

(b) Add 150 mg zinc powder to a solution of 300 mg of the product of Example 1(a) herein in 15 ml acetone and 5 ml water. With stirring, add 300 mg ammonium chloride in four portions during a one hour period at 5°–10°. Allow the reaction mixture to come to room temperature (about 25°). Filter off the zinc, add 100 ml ethylacetate to the filtrate and wash with 2x 50 ml water. Dry the ethylacetate layer over sodium sulfate and concentrate in vacuo to obtain allyl 5R,6S,8R 2-[2-(2-benzothiazole)thio]ethylthio-6-(1-hydroxyethyl)-penem-3-carboxylate.

(c) Under an argon atmosphere add a solution of 39 mg sodium hexanoate in 7 ml ethylacetate to a solution of 111 mg (0.23 m mole) of the product of Example 1(b) herein and 5 mg triphenylphosphine in 3 ml CH$_2$Cl$_2$ (dry). Add to the resulting solution 5 mg tetrakis-(triphenylphosphine)-palladium-(O) and warm gently on a 38° water bath for a minute. Wash the resulting yellow solid precipitate with ethylacetate, and dry to yield the title compound.

The following compounds of this invention can be prepared following the procedures of Example 1 by substituting equivalent amounts of the appropriate heterocyclic- or aryl-thio for the benzothiazole thiol reactant.

1. Sodium (5R,6S,8R)-2-[2-(5-(1-carboxymethyl tetrazolyl))thio]-ethylthio-6-(1-hydroxyethyl)penem-3-carboxylate.
2. Sodium (5R,6S,8R)-2-[2-(2-imidazolyl)thio]-ethylthio-6-(1-hydroxyethyl)penem-3-carboxylate.
3. Sodium (5R,6S,8R)-2-2-[2-(4-hydroxy)-pyrimidyl)-thio]-ethylthio-6-(1-hydroxyethyl)penem-3-carboxylate.
4. Sodium (5R,6S,8R)-2-2-[2-(6-hydroxy)pyrimidyl]thio]-ethylthio-6-(1-hydroxyethyl)penem-3-carboxylate.

EXAMPLE 2

Sodium (5R,6S,8R)-2[(2-phenylthio)ethylthio]-6-(1-hydroxyethyl)penem-3-carboxylate (a) Add at room temperature 0.03 ml of tri-normalbutyl phosphine to a solution of 50 mg allyl5R,6S,8R-2-(2-hydroxyethyl)thio-6-(1-trichlorolethoxycarbonyloxyethyl)-penem-3-carboxylate and 26.2 mg diphenyldisulfide in 2 ml of dry CH$_2$Cl$_2$. The reaction is complete when TLC (10% Ethylacetate/chloroform) shows no starting material. The product is allyl 5R,6S,8R-2-[(2-phenylthio)ethylthio]-6-(1-trichloroethoxycarbonyloxyethyl)penen-3-carboxylate which is then deprotected at the hydroxy and carboxyl groups as follows:

(b) Add 100 mg of zinc powder to a solution of 212 mg of the product of Example 2(a) in 10 ml acetone and 5 ml water. Then, with stirring, add 200 mg ammonium chloride in 4 portions over 1 hour at 5°–10°. Allow to come to room temperature. The reaction is complete when TLC (10% Ethylacetate/chloroform) shows essentially no starting compound. Filter the zinc off and add 100 ml ethylacetate to the filtrate. Wash with 2X 50 ml of water and dry the organic layer over sodium sulfate then concentrate in vacuo to give the hydroxy deprotected product allyl 5R,6S,8R-2-[(2-phenylthio)ethylthio]-6-(1-hydroxyethyl)penem-3-carboxylate.

(c) Under an argon atmosphere add a solution of 51 mg sodium ethyl hexanoate in 2.5 ml dry ethylacetate to a solution of 130 mg (0.3 m mole) of the product of Example 2(b) and 6 mg of triphenylphosphine in 1 ml CH$_2$Cl$_2$ (dry). Add to the resulting solution 5 mg of tetrakis-(triphenylphosphine)palladium-(O) and mix well. Warm gently in a 40° water bath for 2 hours. A precipitate forms gradually. Extract the reaction mixture with 25 ml water and lyophilize to yield the title compound as a yellow solid.

The following compounds of this invention can be prepared following the procedures of Example 2 by substituting equivalent amounts of the appropriate diaryldisulfide for the diphenyldisulfide reactant.

1. Sodium (5R,6S,8R)-2-[2-(5-(1-ethyl)tetrazolyl))thio]-ethylthio-6-(1-hydroxyethyl)penem-3-carboxylate.
2. Sodium (5R,6S,8R)-2-[2-(2-(2-thiazolyl))-thio]-ethylthio-6-(1-hydroxyethyl)penem-3-carboxylate.
3. Sodium (5R,6S,8R)-2- 2-[2-(4,5-dihydroxy-1-methyl)imidazolylthio]-ethylthio-6-(1-hydroxyethyl)penem-3-carboxylate.
4. Sodium (5R,6S,8R)-2- 2-[2-(4-amino)pyrimidylthio]-ethylthio-6-(1-hydroxyethyl)penem-3-carboxylate.
5. Sodium (5R,6S,8R)-2- 2-[2-(6-amino)pyrimidylthio]-ethylthio-6-(1-hydroxyethyl)penem-3-carboxylate.
6. Sodium (5R,6S,8R) [2-(2-hydroxyphenyl)thio]-ethylthio-6-(1-hydroxyethyl)penem-3-carboxylate.
7. Sodium (5R,6S,8R)-2-(2-naphthylthio)ethylthio-6-(1-hydroxyethyl)penem-3-carboxylate.

EXAMPLE 3

Sodium (5R,6S,8R)-2-[2-(5-(1-methyltetrazolyl)thio]ethylthio -6-(1-hydroxyethyl)penem-3-carboxylate (a) Add, with stirring at about 5°, 0.025 ml diethylazodicarboxylate to a solution of 50 mg allyl (5R,6S,8R)-2-(2-hydroxyethyl)thio-6-(1-trichloroethoxycarbonyloxyethyl)-penem-3-carboxylate and 14 mg 5-(1-methyltetrazolyl)-thiol in 5 ml CH$_2$Cl$_2$. When the reaction is complete in about 2 hours as evidenced when TLC (10% ethylacetate/CH$_2$CL$_2$) shows no starting compound, concentrate the reaction mixture in vacuo and separate the product by TLC to give allyl (5R,6S,8R)-2-[2-(5-(1-methyl-tetrazolyl)thio]ethyl-thio-6-(1-trichloroethoxycarbonyloxyethyl)-penem-3-carboxylate, then deprotect the product, first at the hydroxy group, then at the carboxyl group as follows:

(b) Add 130 mg zinc powder to a solution of 260 mg of the compound made in Example 3(a) in 15 ml acetone and 5 ml water. Add, with stirring, 250 mg ammonium chloride in four portions over one hour at 5°-10°. Allow to come to room temperature to complete the reaction which is evidenced by TLC (10% ethylacetate/CH$_2$CL$_2$) showing essentially no starting material. Filter off the zinc and add 100 ml ethylacetate to the filtrate. Wash with 2X 50 ml water. Dry the ethylacetate layer and concentrate in vacuo. Separate the product by TLC to give allyl (5R,6S,8R)-2-[2-(5-(1-methyl-tetrazolyl)thiol]-ethylthio-6-(1-hydroxyethyl)-penem-3-carboxylate.

(c) Under an argon atmosphere add a solution of 47 mg sodium hexanoate in 7 ml ethylacetate (dry) to a solution of 120 mg (0.28 m mole) of the compound produced in Example 3(b) herein and 5.5 mg of triphenylphosphine in 3 ml dry CH$_2$Cl$_2$. Add to the resulting solution 5 mg of tetrakis-(triphenylphosphine) palladium-(O) and warm the resulting mixture briefly on a 38° water bath. The reaction is complete in about 5 minutes when a yellow precipitate forms and TLC shows no starting compound. Collect the product, wash with ethylacetate and dry at room temperature under vacuum to give the title compound as a yellow solid.

The following compounds of this invention can be prepared following the procedures of Example 3 by substituting equivalent amounts of the appropriate heterocyclic or aryl thiol for the 5-(1-methyltetrazolyl)-thiol reactant.

1. Sodium (5R,6S,8R)-2-[2-(5-(1-β-dimethylaminoethyl tetrazolyl)thio]-ethylthio-6-(1-hydroxyethyl)penem-3-carboxylate.
2. Sodium (5R,6S,8R)-2-[2-(5-tetrazolyl)thio]-ethylthio-6-(1-hydroxyethyl)penem-3-carboxylate.
3. Sodium (5R,6S,8R)-2-[2-(4-1,2,3-triazolyl)-thio]-ethylthio-6-(1-hydroxyethyl)penem-3-carboxylate.
4. Sodium (5R,6S,8R)-2-[2-(5-1,2,3-triazolyl)-thio]-ethylthio-6-(1-hydroxyethyl)penem-3-carboxylate.

EXAMPLE 4

Sodium (5R,6S,8R)-2[2-(2-(1-methylimidazole)thio]ethylthio-6-(1-hydroxymethyl)penem-3-carboxylate (a) Add 56.4 mg of trifluoro methane sulfonic anhydride at −10° to a stirred solution at −10° of 100 mg allyl-5R,6S,8R-2-(2-hydroxyethyl)thio-6-(1-trichloro ethoxycarbonyloxyethyl)-penem-3-carboxylate and 30 mg pyridine in 5 ml dry methylenechloride. Add to the resulting reaction mixture 50 mg of anhydrous potassium carbonate followed by a solution of 26 mg 1-methyl-2-mercaptoimidazole in 1 ml methylenechloride and stir for about one-half hour at −10° to −5°. The reaction is complete when TLC (50% ethylacetate/methylenechloride) shows essentially no starting material. Pour the reaction mixture into ice-water, separate the methylenechloride and dry it with sodium sulfate. Concentrate and separate the product by TLC to give allyl (5R,6S,8R)-2-[2-(2-(1-methylimidazole)thio]ethylthio-6-(1-tri-chloroethoxycarbonyloxyethyl)penem-3-carboxylate. Deprotect the product, first at the hydroxy group, then at the carboxyl group as follows:

(b) Add 0.06 ml glacial acetic acid to a stirred and cooled (5°) solution of 250 mg of the product of Example 4(a) herein in 1 ml CH$_2$Cl$_2$ and 1 ml isopropyl alcohol. Stir for 15 minutes and add 50 mg zinc dust. Stir for three hours at 10°-15°. Filter off the zinc, and recover the product allyl (5R,6S,8R)-2-[2-(2-[1-methylimidazolyl)thiol]ethylthio-6-(1-hydroxyethyl)-penem-3-carboxylate.

(c) Under an argon atmosphere add a solution of 50.8 mg sodium hexanoate in 9 ml ethylacetate to a solution of 133 mg (0.31 m mole) of the product of Example 4(b) herein and 6.5 mg triphenylphosphine in 4 ml CH$_2$Cl$_2$ (dry). Add to the resulting solution 6.5 mg tetrakis-(triphenylphosphine)-palladium-(O) and warm gently on a 38° water bath for about a minute. Wash the resulting precipitate with ethylacetate and dry to yield the title compound.

The following compounds of this invention can be prepared following the procedures of Example 4 and 5 by substituting equivalent amounts of the appropriate heterocyclic or aryl thiol for the 1-methyl-2-mercaptoimidazole reactant.

1. Sodium (5R,6S,8R)-2-[2-(2-(2-thiazolyl))-thio]-ethylthio-6-(1-hydroxyethyl)penem-3-carboxylate.
2. Sodium (5R,6S,8R)-2- 2-[2-(1,3,4thiadiazolylthio]-ethylthio-6-(1-hydroxyethyl)penem-3-carboxylate.

3. Sodium (5R,6S,8R)-2- 2-[2-(3-methyl)1,3,4-thiadiazolylthio]-ethylthio-6-(1-hydroxyethyl)-penem-3-carboxylate.
4. Sodium (5R,6S,8R)-2-[2-(2-pyrimidyl)thio]-ethylthio-6-(1-hydroxyethyl)penem-3-carboxylate.
5. Sodium (5R,6S,8R)-2-[2-(2-furyl)thio]-ethylthio-6-(1-hydroxyethyl)penem-3-carboxylate.
6. Sodium (5R,6S,8R)-2-[2-(2-pyrryl)thio]-ethylthio-6-(1-hydroxyethyl)penem-3-carboxylate.
7. Sodium (5R,6S,8R)-2-(2-phenylthio)-ethylthio-6-(1-hydroxyethyl)penem-3-carboxylate.

EXAMPLE 5

Sodium (5R,6S,8R)-2-[2-(3-hydroxypyridyl)thio]ethylthio-6-(1-hydroxyethyl)penem-3-carboxylate (a) Add 56.4 mg of trifluoromethano sulfonic anhydride at −10° to a stirred solution at −10° of 200 ml allyl-(5R,6S,8R)-2-(2hydroxyethyl)thio-6-(1-trichloroethoxycarbonyloxyethyl)-penem-3-carboxylate and 30 mg pyridine in 3 ml CH$_2$Cl$_2$. Stir for fifteen minutes at 0° to −10°. Add to the resulting reaction mixture 50 mg of anhydrous potassium carbonate followed by 28 mg of 3-hydroxy-2-mercapto pyridine. Stir the reaction mixture for about one hour at −5° to −10° and then allow it to slowly come to room temperature. The reaction is complete when TLC (15% ethylacetate/CH$_2$Cl$_2$) shows essentially no starting material. The product is separated by TLC to yield allyl (5R,6S,8R)-2-[2-2(3-hydroxypyridyl)-thio]ethylthio-6-(1-trichloroethoxycarbonyloxyethyl)penem-3-carboxylate. Deprotect the product, first at the hydroxy group, then at the carboxyl group as follows:

(b) Add 0.07 ml glacial acetic acid to a stirred and cooled (5°) solution of 300 mg of the product of Example 5(a) in 1 ml CH$_2$Cl$_2$ and 1 ml isopropyl alcohol. Stir for 15 minutes and add 30 mg activated zinc powder. Stir for 1 hour at 10°–15°. Filter off the zinc and wash with 50 ml ethylacetate and 25 ml water with CaCO$_3$. Dry the ethylacetate layer over sodium sulfate and concentrate in vacuo to obtain allyl(5R,6S,8R)-2[2-(2-(3-hydroxypyridyl)-thio]ethylthio6-(1-hydroxyethyl)-penem-3-carboxylate as a yellow oil.

(c) Under an argon atmosphere add a solution of 42 mg sodium hexanoate in 7 ml ethylacetate to a solution of 113 mg (0.25 m mole) of the product of Example 5(b) herein and 5 mg triphenylphosphine in 3 ml dry CH$_2$Cl$_2$. Add to the resulting solution 5 mg tetrakis-(triphenylphosphine)-palladium-(O) and warm gently on a 38° water bath for about a minute. Wash the resulting precipitate with ethylacetate and dry to yield the title compound.

EXAMPLE 6

Sodium (5R,6S,8R)-2-[2-(2-benzimidazolyl)thio]-ethylthio-6-(1-hydroxyethyl)penem-3-carboxylate (a) Add 56.4 mg of trifluoromethane sulfonic anhydride at −10° to a stirred solution at −10° of 100 mg allyl-(5R,6S,8R)-2-(2-hydroxyethyl)thio-6-(1-trichloroethoxy carbonyloxyethyl)-penem-3-carboxylate and 30 mg pyridine in 3 ml CH$_2$Cl$_2$. Stir for 15 minutes at about −10°. Add to the reaction mixture 50 mg of anhydrous potassium carbonate followed by 33 mg of 2 mercaptobenzimidazole which is insoluble in the reaction mixture. Stir the reaction mixture for about one-half hour at about −10°. Add 1 ml dry tetrahydrofuran (THF) whereupon TLC (15% ethylacetate/CH$_2$Cl$_2$) shows the reaction is completed since essentially no starting material is shown. The product is separated by TLC to yield allyl (5R,6S,8R)-2-[2-(2-benzimidazolyl)thio]-ethylthio-6-(1-trichloro ethoxycarbonyloxyethyl)-penem-3-carboxylate. Deprotect the product, first at the hydroxy group, then at the carboxyl group as follows:

(b) Add 0.06 ml glacial acetic acid to a solution of 258 mg of the product of Example 6(a) herein in 1 ml CH$_2$Cl$_2$ and 1 ml isopropyl alcohol. Add 50 mg active zinc and stir at 15° for about one hour. Filter off the zinc, add 25 ml ethylacetate to the filtrate and wash with water, dry the ethyl acetate layer over sodium sulfate and concentrate in vacuo to obtain allyl (5R,6S,8R)2-[2-(2-benzimidazolyl)thio]ethylthio-6-(1-hydroxyethyl)penem-3-carboxylate.

(c) Under an argon atmosphere add a solution of 19.7 mg sodium hexanoate in 3 ml ethylacetate to a solution of 54 mg of the product of Example 6(b) herein and 15 mg triphenylphosphine in 1.5 ml dry CH$_2$Cl$_2$. Add to the resulting solution 5 mg tetrakis(triphenyl phosphine)-palladium-(O) and warm gently on a 38° water bath for about 15 minutes. Wash the resulting precipitate with ethylacetate and dry to yield the title compound.

The following compounds of the invention can be prepared following the procedure of Example 6 using a tetrahydrofuran solvent in step (a) to solubilize the starting heterocyclic or aryl thio compounds which are insoluble in methylene chloride, by substituting equivalent amounts of the appropriate heterocyclic or aryl thiol for the 1-mercaptobenzimidazole reactant.

1. Sodium (5R,6S,8R)-2-[2-((5-thiazolyl))thio]-ethylthio-6-(1-hydroxyethyl)penem-3-carboxylate.
2. Sodium (5R,6S,8R)-2-[2-(2-(thiazolyl))thio]-ethylthio-6-(1-hydroxyethyl)penem-3-carboxylate.
3. Sodium (5R,6S,8R)-2-[2-(2-(pyridyl))thio]-ethylthio-6-(1-hydroxyethyl)penem-3-carboxylate.
4. Sodium (5R,6S,8R)-2-[2-((4-pyridyl))thio]ethylthio-6-(1-hydroxyethyl)penem-3-carboxylate.
5. Sodium (5R,6S,8R)-2-[2-(2-(4-hydroxy)pyridyl)thio]-ethylthio-6-(1-hydroxyethyl)penem-3-carboxylate.
6. Sodium (5R,6S,8R)-2-2-[2-(6-hydroxy)pyridyl)thio]-ethylthio-6-(1-hydroxyethyl)penem-3-carboxylate.
7. Sodium (5R,6S,8R)-2-2-[2-(3-amino)pyridyl)thio]-ethylthio-6-(1-hydroxyethyl)penem-3-carboxylate.
8. Sodium (5R,6S,8R)-2-[2-(4-amino)pyridyl)thio]-ethylthio-6-(1-hydroxyethyl)penem-3-carboxylate.
9. Sodium (5R,6S,8R)-2-2-[2-(6-amino)-pyridyl)thio]-ethylthio-6-(1-hydroxyethyl)penem-3-carboxylate.
10. Sodium (5R,6S,8R)-2-2-[(4-(2-hydroxy)pyridyl)thio]-ethylthio-6-(1-hydroxyethyl)penem-3-carboxylate.
11. Sodium(5R,6S,8R)-2-2-[(4-(2-amino)-pyridyl)thio]-ethylthio-6-(1-hydroxyethyl)penem-3-carboxylate.
12. Sodium (5R,6S,8R)-2-[2-(2-purinyl)thio]-ethylthio-6-(1-hydroxyethyl)penem-3-carboxylate.
13. Sodium (5R,6S,8R)-2-2-[2-(4-hydroxy)purinylthio]-ethylthio-6-(1-hydroxyethyl)penem-3-carboxylate.
14. Sodium (5R,6S,8R)-2-2-[2-(8-hydroxy)purinylthio]-ethylthio-6-(1-hydroxyethyl)penem-3-carboxylate.
15. Sodium (5R,6S,8R)-2-2[2-(4-amino)-purinylthio]-ethylthio-6-(1-hydroxyethyl)penem-3-carboxylate.
16. Sodium (5R,6S,8R)-2-2-[2-(8-amino)-purinylthio]-ethylthio-6-(1-hydroxyethyl)penem-3-carboxylate.
17. Sodium (5R,6S,8R)-2-[2-(8-purinyl)thio]-ethylthio-6-(1-hydroxyethyl)penem-3-carboxylate.

18. Sodium (5R,6S,8R)-2-2-[8-(2-hydroxy)-purinylthio]-ethylthio-6-(1-hydroxyethyl)penem-3-carboxylate.
19. Sodium (5R,6S,8R)-2-2-[8-(4-hydroxy)-purinylthio]-ethylthio-6-(1-hydroxyethyl)penem-3-carboxylate.
20. Sodium (5R,6S,8R)-2-2-[8-(2-amino)-purinylthio]-ethylthio-6-(1-hydroxyethyl)penem-3-carboxylate.
21. Sodium (5R,6S,8R)-2-2-[8-(4-amino)-purinylthio]-ethylthio-6-(1-hydroxyethyl)penem-3-carboxylate.
22. Sodium (5R,6S,8R)-2-2-[3-(5,6 dioxo)1-2-4-triazinylthio]-ethylthio-6-(1-hydroxyethyl)penem-3-carboxylate.
23. Sodium (5R,6S,8R)-2-2-[3-(5,6 dioxo)2-methyl-1,2,6 triazinylthio]-ethylthio-6-(1-hydroxyethyl)penem-3-carboxylate.
24. Sodium (5R,6S,8R)-2-[2-(2-thienyl)thio]-ethylthio-6-(1-hydroxyethyl)penem-3-carboxylate.
25. Sodium (5R,6S,8R)-2-[2-(2-oxazinyl)thio]-ethylthio-6-(1-hydroxyethyl)penem-3-carboxylate.

In the following examples which exemplify some of the dosage formulations in which the compounds of this invention may be employed, the active ingredient is designated by the term "Drug" which is meant to indicate one of the following compounds Sodium (5R,6S,8R)-2-[2-(2-benzothiazole)-thio]ethylthio-6-(1-hydroxyethyl)penem-3-carboxylate.
Sodium (5R,6S,8R)-2[(2-phenylthio)ethylthio]-6-(1-hydroxyethyl)penem-3-carboxylate.
Sodium (5R,6S,8R)-2-[2-(5-(1-methyltetrazolyl)thio]ethylthio-6-(1-hydroxyethyl)penem-3-carboxylate.
Sodium (5R,6S,8R)-2-[2-(2-1-methylimidazole) thio]-ethylthio-6-(1-hydroxymethyl)penem-3-carboxylate.
Sodium (5R,6S,8R)-2-[2-(2-(3-hydroxypyridyl))thio]ethylthio-6-[2-(1-hydroxyethyl)penem-3-carboxylate.
Sodium (5R,6S,8R)-2-[2-(2-(benzimidazolyl))thio]-ethylthio-6-(1-hydroxyethyl)penem-3-carboxylate.

It will be appreciated that each of these compounds may be replaced by equivalent effective amounts of the other compounds of formula I.

EXAMPLE 7

| Oral formulation | |
|---|---|
| Drug | 250.0 mg |
| Lactose | 148.0 mg |
| Magnesium stearate | 2.0 mg |
| | 400.0 mg |

Blend the ingredients and fill into hard gelatin capsules.

EXAMPLE 8

Intravenous forumulation

Asceptically add 5 ml of sterile water for injection to a vial containing sterile powder of the Drug and sterile water for injection U.S.P., and withdraw entire contents.

We claim:
1. A compound represented by the formula

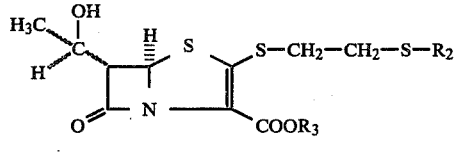

wherein $R_2$ represents a substituted or unsubstituted single ring or double fused ring aryl or heterocyclyl radical bonded to the sulfur atom by a ring carbon, selected from the group consisting of substituted phenyl, naphthyl, benzothiazolyl, oxazinyl, pyridyl, purinyl, imidazolyl, pyrryl, thiazolyl, thiadiazolyl, benzamidazolyl, triazinyl, furyl, thienyl, thiazinyl, triazolyl, tetrazolyl and pyrimidyl, wherein when substituted, said aryl or heterocyclic rings have one or more substituent which can be the same or different
(a) are on a ring carbon or heteroatom, and are independently selected from the group consisting of lower alkyl,

and loweralkylene

wherein $R_4$ and $R_5$ are the same or different and are independently selected from the group consisting of hydrogen, halogen and lower alkyl or
(b) are on a ring carbon atom only and are selected from the group consisting of =O, hydroxy, lower alkoxy, —COOR$_3$ or halogen;
$R_3$ represents hydrogen, a pharmaceutically acceptable readily metabolizable ester-forming substituent or a pharmaceutically acceptable cation; and the wavy line indicates either the 5R,6S,8R or 5R,6R,8S stereoisomers.

2. A compound of claim 1 which is the 5R,6S,8R stereoisomer.
3. A compound of claim 2 wherein $R_2$ represents 2-benzothiazolyl and $R_3$ represents sodium, i.e. Sodium (5R,6S,8R)-2-[2(2-benzothiazolyl)-thio]ethylthio-6-(1-hydroxyethyl)-penem-3-carboxylate.
4. A compound of claim 2 wherein $R_2$ represents 5-(1-methyltetrazolyl) and $R_3$ represents sodium, i.e. Sodium (5R,6S,8R)-2-[2-(5-(1-methyltetrazolyl)thio]ethylthio]-6-(1-hydroxyethyl)penem-3-carboxylate.
5. A compound of claim 2 wherein $R_2$ represents 2-(1-methylimidazolyl) and $R_3$ represents sodium, i.e. Sodium(5R,6S,8R)-2[2-(2-methylimidazolyl)thio]ethylthio-6-(1-hydroxyethyl)penem-3-carboxylate.
6. A compound of claim 2 wherein $R_2$ represents 2-(3-hydroxypyridyl) and $R_3$ represents sodium, i.e. Sodium (5R,6S,8R)-2-[2-(2-(3-hydroxypyridyl))thio]ethylthio-6-(1-hydroxyethyl)penem-3-carboxylate.
7. A compound of claim 2 wherein $R_2$ represents 2-benzoimidazolyl and $R_3$ represents sodium, i.e. Sodium (5R,6S,8R)-2-[2-(2-(benzimidazolyl))thiol]-ethylthio-6-(1-hydroxyethyl)-penem-3-carboxylate.
8. A compound represented by the formula

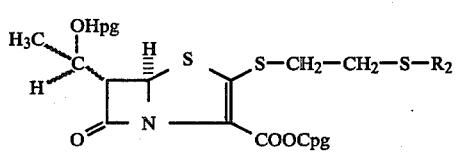

wherein $R_2$ and the wavy lines are as defined in claim 1; Cpg represents a readily removable carboxyprotecting group; and Hpg represents a readily removable hydroxyprotecting group.

9. A compound of claim 8 which is the 5R,6S,8R stereoisomer in which Hpg represents 2,2,2-trichloroethoxycarbonyl and Cpg represents allyl.

10. A pharmaceutical composition comprising an antibacterially effective amount of a compound of claim 1 together with a non-toxic pharmaceutically acceptable carrier.

11. An oral dosage composition of claim 10.

12. A parenteral composition of claim 10.

13. a composition of claim 11 which is a capsule.

14. A method of eliciting an antibacterial response in a warm-blooded animal having a susceptible bacterial infection which comprises administering to said animal a non-toxic, antibacterially effective amount of a compound of claim 1.

* * * * *